United States Patent [19]

Suda et al.

[11] 3,932,528

[45] Jan. 13, 1976

[54] PROCESS FOR THE SEPARATION OF DIHYDROPEROXIDES

[75] Inventors: Hideaki Suda, Takaishi; Iwao Dohgane, Nishinomiya; Takashi Chinuki, Toyonaka; Kenji Tanimoto; Hirokazu Hosaka, both of Minoo; Yukimichi Nakao, Kobe; Yuji Ueda, Izumiotsu; Seiya Imada, Sakai; Hideki Yanagihara, Toyonaka; Kunihiko Tanaka, Ibaragi, all of Japan

[73] Assignee: Sumitomo Chemical Company, Limited, Osaka, Japan

[22] Filed: Aug. 27, 1973

[21] Appl. No.: 391,873

[30] Foreign Application Priority Data

Sept. 8, 1972 Japan.............................. 47-90568

[52] U.S. Cl............................................ 260/610 A
[51] Int. Cl.²....................................... C07C 179/02
[58] Field of Search ................... 260/610 B, 610 A

[56] References Cited
UNITED STATES PATENTS

| | | | |
|---|---|---|---|
| 2,279,277 | 4/1942 | Shoemaker........................... | 199/43 |
| 2,609,391 | 9/1952 | Greenspan et al.................... | 260/502 |
| 2,618,538 | 11/1952 | Jones................................... | 260/610 A |
| 2,796,439 | 6/1957 | Berneis............................... | 260/610 B |
| 3,160,668 | 12/1964 | Davie et al......................... | 260/610 B |
| 3,645,908 | 2/1972 | Edl et al.............................. | 252/186 |
| 3,847,830 | 11/1974 | Williams et al..................... | 252/186 |

FOREIGN PATENTS OR APPLICATIONS

| | | | |
|---|---|---|---|
| 1,002,357 | 2/1967 | Germany ........................ | 260/610 A |
| 1,032,122 | 6/1966 | United Kingdom............. | 260/610 A |
| 1,289,047 | 2/1969 | Germany ........................ | 260/610 A |
| 692,876 | 8/1964 | Canada............................ | 260/610 A |

*Primary Examiner*—James O. Thomas, Jr.
*Assistant Examiner*—W. B. Lone
*Attorney, Agent, or Firm*—Stevens, Davis, Miller & Mosher

[57] ABSTRACT

Dihydroperoxides of dialkylaromatic hydrocarbons are separated in high yield from an aqueous alkaline solutions of hydroperoxides containing the dihydroperoxides by adding 0.01 to 1 % by weight of a compound having a nitrogen base, such as ammonia and aromatic amines, to the solution, based on the weight of the solution, thereby stabilizing the dihydroperoxides in the solution, and separating the dihydroperoxides therefrom by extraction.

1 Claim, 3 Drawing Figures

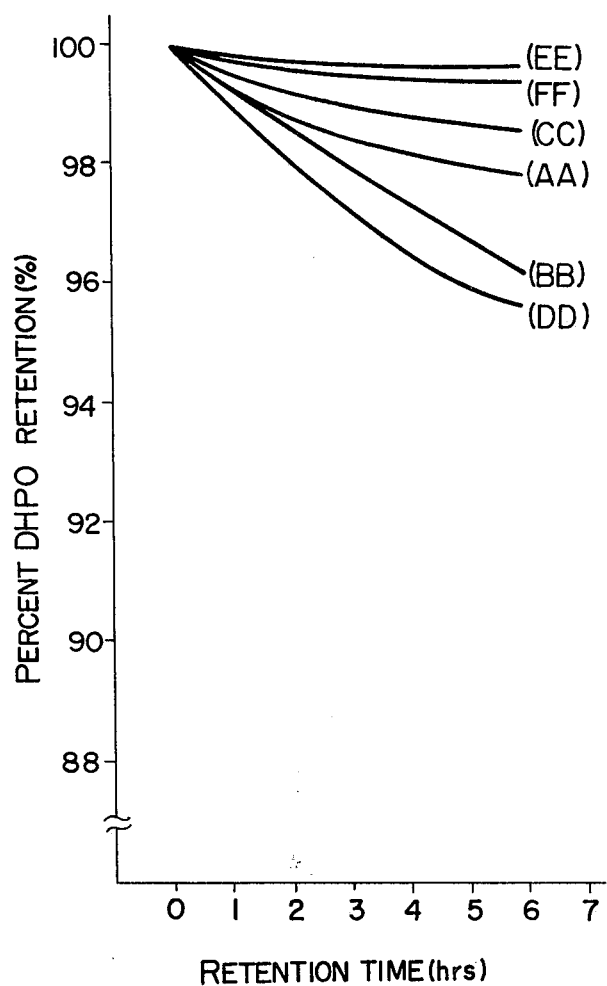

PROCESS FOR THE SEPARATION OF DIHYDROPEROXIDES

This invention relates to a process for separating dihydroperoxides of dialkylaromatic hydrocarbons by extraction from an aqueous alkaline solution containing the dihydroperoxides, and more particularly to a process for stabilizing dihydroperoxides of dialkylaromatic hydrocarbon represented by the general formula:

$$R_1 - Ar - R_2$$

wherein $R_1$ and $R_2$ are alkyl groups having three to four carbon atoms and Ar an aromatic group, (the dihydroperoxides will be hereinafter referred to as DHPO) in the process for separating DHPO from an aqueous alkaline solution containing DHPO by extraction, which comprises adding a compound having a nitrogen base to the solution, thereby increasing a percent retention of DHPO in the solution, and separating DHPO in a good yield even at a high temperature by extraction. The percent retention is a ratio of an amount of a specific substance in a solution after some treatment to that before treatment, for example, represented by a formula B/A, when an amount A of the specific substance in a solution before treatment is changed to an amount B by some treatment.

When dialkylaromatic hydrocarbons are oxidized by ordinary procedure with oxygen or air, monohydroperoxides (which will be hereinafter referred to as MHPO), DHPO and several other kinds of hydroperoxides (which will be hereinafter referred to as HPO) of dialkylaromatic hydrocarbons are produced at the same time.

It is necessary to effectively separate or recover MHPO and DHPO from the resulting oxidation product solution containing these hydroperoxides. For example, the recovered MHPO is recycled to the oxidation reaction to convert it to DHPO. The recovered DHPO is subjected to cleavage reaction with an acid catalyst, for example, sulfuric acid, etc. to obtain the corresponding divalent phenols.

To carry out the successive cleavage reaction smoothly in good yield, it is an essential condition to effectively separate DHPO from these HPO compounds.

It is known from British Patent Specification No. 727498 to separate MHPO and DHPO from the oxidation product solution containing HPO compounds, that is, MHPO, DHPO and HPO by treating the solution with an aqueous 4–15 wt. % alkali solution (% hereinafter referred to is all by weight).

Said prior art process has a good selectivity on one hand, as compared with other separation processes, but has the following two disadvantages on the other hand: Firstly, the stability of MHPO is poor in an aqueous alkaline solution, and secondly DHPO cannot be extracted as such (see Japanese Patent Publication No. 521/56).

Among these two disadvantages, the first problem can be solved by treating the solution at a low temperature. Loss of MHPO can be repressed thereby to a minimum within a substantially permissible range without so much reduction in selectivity. Therefore, the first problem is not so serious disadvantage.

As to the second problem, there has been known a process for extracting DHPO from an aqueous alkaline solution containing DHPO with an organic solvent and using DHPO as such (see German Patent No. 1,134,375), and the problem seems as if it has been solved. However, the percent retention of DHPO in the aqueous alkaline solution still remains as a serious problem in that case, and thus said disadvantage has not yet been overcome completely. The present inventors have thought highly of the aqueous alkaline solution treatment, because said treatment has a distinguished selectivity never comparable with other processes, and thus have made studies on an improvement of disadvantages of the aqueous alkaline solution treatment so as to fully take advantage of the superiority of the aqueous alkaline solution treatment. As a result, the present inventors have confirmed that said disadvantages have not yet been overcome completely, though various attempts and researches have been so far carried out to improve said disadvantages. Especially, low percent retention of DHPO in the aqueous alkaline solution is a fatal disadvantage, and it can be said that the effectiveness of the aqueous alkaline solution treatment depends solely upon an improvement of the low percent retention. That is, according to the conventional aqueous alkaline solution treatment, it is impossible to separate DHPO to obtain it as such. That is, a complicated step of making the resulting DHPO free by acid or through extraction by specific organic solvents, for example, methylethylketone, methylisobutylketone, etc. is further necessary. However, in the latter case, it is hard to extract DHPO into an organic layer with ease, because DHPO takes a salt-like form in the aqueous alkaline solution, and an extraction treatment at a considerably high temperature is necessary for obtaining DHPO as such. For example, the extraction treatment is carried out at 75°C in said German Patent. However, the stability of DHPO is quite poor in the aqueous alkaline solution, and is quite adversely influenced particularly by temperature.

The present inventors have made various studies on how to prevent the DHPO loss on the basis of these confirmed facts, and, as a result, have found that addition of a compound having a nitrogen base to the aqueous alkaline solution containing DHPO has a remarkable effect upon the percent DHPO retention even at a high temperature without giving any influence upon the extraction efficiency.

The alkylaromatic compounds referred to in the present invention include, for example, diisopropylbenzene, di-sec-butylbenzene, diisobutylenzene, etc., and particularly diisopropylbenzene is a well known compound as a raw material for producing resorcinol, hydroquinone, etc.

Examples of the compounds having a nitrogen base, as referred to herein, include ammonia, aniline, toluidine, diphenylamine, N-methylaniline, N, N-dimethylaniline, benzylamine, α-phenylethylamine, triethylamine, pyridine, urea, etc. These compounds having the nitrogen base are all effective for the purpose of the present invention, but particularly ammonia and aromatic amines are suitable for the present invention. These compounds having the nitrogen base are effective for increasing the percent DHPO retention of the aqueous alkaline solution and have no influence at all upon the extraction efficiency of DHPO.

That is, the addition of a compound having a nitrogen base has no influence upon the extraction efficiency of DHPO, when DHPO is extracted into an aqueous alkaline layer from the oxidation product solution containing DHPO with the aqueous alkaline solution, or when DHPO is extracted from the aqueous alkaline solution containing DHPO with an organic solvent. However, the addition of the compound having a nitrogen base has a large effect upon the increase in the percent DHPO retention of the aqueous alkaline solution, and it is obvious that the addition of a compound having a nitrogen base to the solution consequently gives a very advantageous effect upon the extraction of DHPO from the solution.

The amount of the compound having the nitrogen base somewhat depends upon the kind of the compound, but in almost all the cases, it is effective to add 0.01 to 1% of the compound to an aqueous alkaline solution containing DHPO, based on the weight of the solution.

Now, the present invention will be described by way of the accompanying drawings.

FIG. 3 shows a relation between the retention time (hr) and percent DHPO retention in the case that compounds having a nitrogen base are added to the reaction solution.

Figure 1:
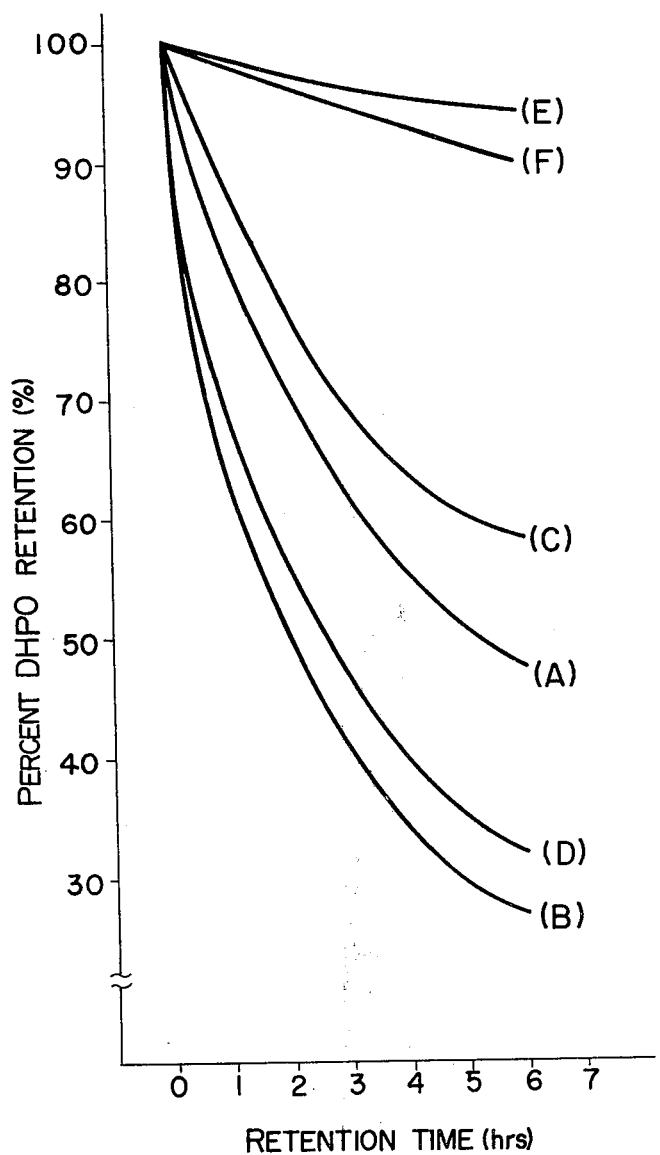
FIG. 1 shows a relation between the retention time (hr) and the percent DHPO retention in the case that no compound having a nitrogen base is added to the reaction solution.

The present inventors carried out tests on the percent DHPO retention in aqueous alkali solutions of oxidation products containing HPO compounds of diisopropylbenzene, that is, aqueous alkali solutions especially prepared for separating DHPO, and obtained the results as shown in FIG. 1.

The percent DHPO retention as referred to herein is calculated by the following formula:

Percent DHPO retention (%)

$$= \frac{\text{Amount of DHPO remaining in oxidation product solution after treatment}}{\text{Amount of DHPO contained in oxidation product solution before treatment}} \times 100$$

More concretely, the aforesaid formula can be rewritten as follows;
Percent DHPO retention (%) = 100 − Loss* DHPO (%) = Extract DHPO (%) = DHPO in the aqueous layer (%).
The loss is due to the decomposition, but not to the handling.

That is, Test (1) was carried out to determine the percent DHPO retentions for various retention times when an aqueous 8% caustic soda solution containing 12.3% DHP was retained at 60°C with heating [shown as (A) in FIG. 1]. Test (2) was carried out to determine the percent DHPO retentions for various retention times when an aqueous 8% caustic soda solution containing 12.3% DHPO was again prepared by adding freshly DHPO and caustic soda to the aqueous caustic soda solution used in the test (1) (the caustic soda recycled will be hereinafter referred to as "recycle caustic soda"), and retained at 60°C with heating [shown as (B) in FIG. 1]. Likewise, Tests (3) was carried out to determine the percent DHPO retention for an aqueous 12.3% DHPO – 4% caustic soda solution retained at 60°C [shown as (C) in FIG. 1] Test (4) for an aqueous 12.3% DHPO – 4% recycle caustic soda solution retained at 60°C [shown as (D) in FIG. 1] Test (5) for an aqueous 12.3% DHPO – 8% caustic soda solution retained at 30° C [shown as (E) in FIG. 1] and Test (6) for an aqueous 12.3% DHPO – 8% recycle caustic soda solution retained at 30°C [shown as (F) in FIG. 1].

In the case of Tests (5) and (6), shown as (E) and (F) in FIG. 1, the percent DHPO retention was high at a low temperature, but when an extraction operation was carried out at that temperature (30°C), the extraction efficiency was very low. That is, when the extraction and separation of DHPO are evaluated in view of a combination of the percent DHPO retention and the extraction efficiency, yield of DHPO is very low, and an industrial scale extraction of DHPO is therefore uneconomical and cannot be carried out.

Further, in the case of Tests (1) to (4), shown as (A) to (D) in FIG. 1, the percent DHPO retention is low, but the extraction efficiency of DHPO is high on account of high temperature (60°C). However, its yield is also low in view of a combination of the percent DHPO retention and the extraction efficiency.

It is the well known fact that the extraction efficiency is increased with higher temperature, and therefore an increase in the percent DHPO retention at a high temperature will be an important factor in the separation of DHPO. On the other hand, the percent DHPO retention is lowered by recyclic use of caustic soda, but the recyclic use must be carried out from the economical viewpoint, if the extraction is carried out, for example, in an industrial scale. In other words, the extraction must be carried out under the most stringent conditions especially for the percent DHPO retention.

For these reasons, the percent DHPO retention will be very low, when DHPO is extracted in s substantially effective form from the oxidation product solution of HPO compounds with the aqueous alkaline solution.

Figure 2:
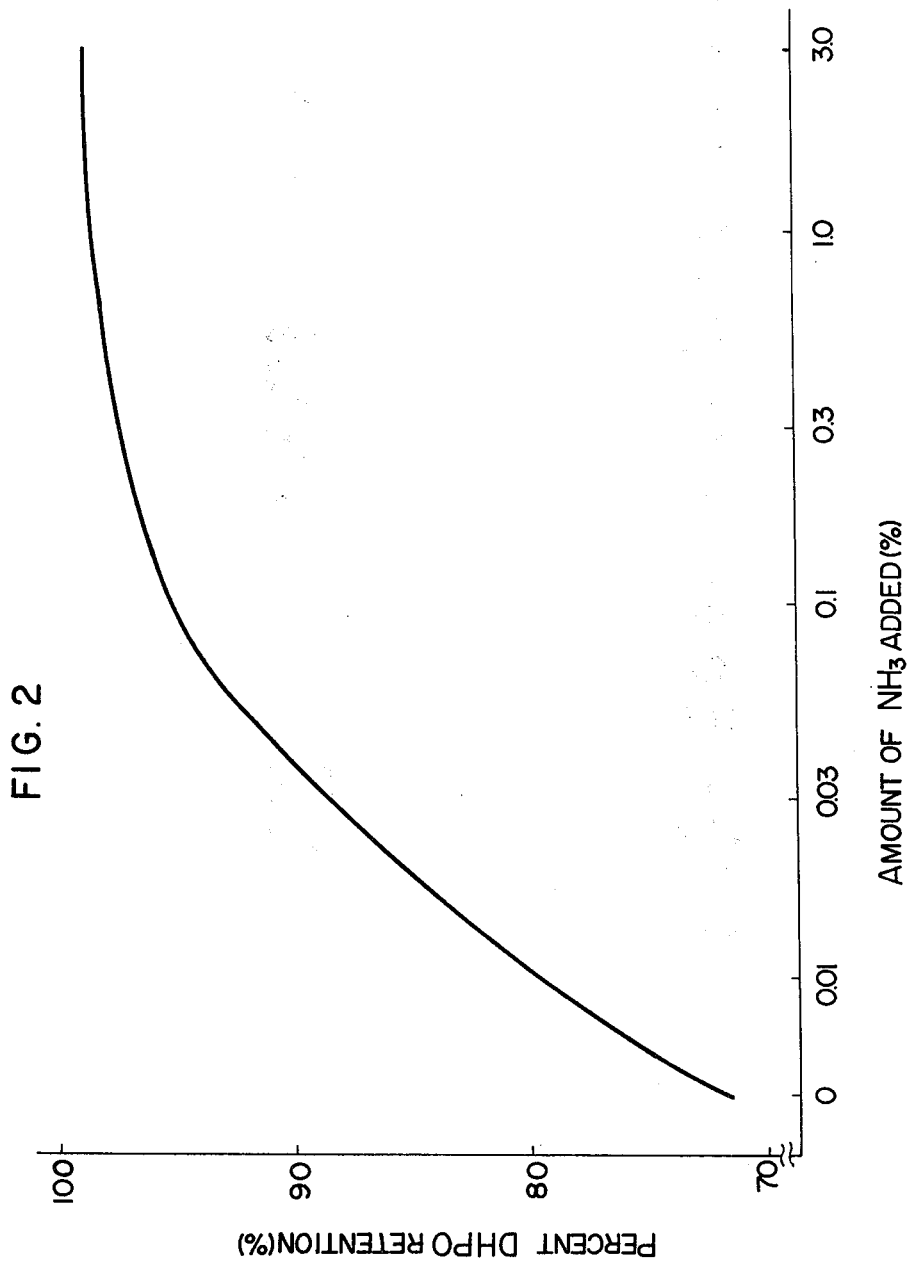
FIG. 2 shows a relation between amounts (%) of ammonia and percent DHPO retention where the retention time is 2 hours, in the case that ammonia is added to the reaction solution.

FIG. 2 shows a relation between amounts of the compound added and the percent DHPO retention by way of ammonia as the compound. The conditions for the test are the same as in said Test (1), and the percent DHPO retention shown in FIG. 2 corresponds to that at the time of 2 hours in FIG. 1.

The addition of the compound having the nitrogen base according to the present invention is not only effective for the most unstable DHPO, but also widely applicable, in general, to the HPO compounds of the same species, if necessary.

Now, the stability of DHPO in the aqueous alkaline solution will be described by way of Reference Example.

REFERENCE EXAMPLE

In correspondence with the foregoing Test (1) to (6), 0.5% of a compound having a nitrogen base was added to the respective solutions, and changes with time in the percent DHPO retention were observed according to the respective procedures shown in FIG. 1.

That is to say, ammonia was added as the compound having the nitrogen base to the same solution as in Test (1) and changes with time in the percent DHPO retention were determined under the same conditions as in Test (1). The result is shown by (AA) in FIG. 3.

Likewise, paratoluidine was added to the solution in correspondence with Test (2) [the result being shown as (BB) in FIG. 3 aniline in correspondence with Test (3) [the result being shown as (CC) in FIG. 3] diphenylamine in correspondence with Test 4 [the result being shown as (DD) in FIG. 3] benzylamine in correspondence with Test (5) [the result being shown as (EE) in FIG. 3] and triethylamine in correspondence with Test (6) [the result being shown as (FF) in FIG. 3].

Comparison in changes in the percent DHPO retention for the equal retention time between FIGS. 1 and 3 reveals that the addition of the compound having the nitrogen base greatly improves the stability of DHPO in the aqueous alkaline solution.

For example, in the case of Test (2) where no compound having the nitrogen base was added, as shown by (B) in FIG. 1, the percent DHPO retention was 27% at the retention time of 6 hours, but when paratoluidine was added thereto, as shown by (BB) in FIG. 3, a percent DHPO retention as high as 96% was obtained at the equal retention time even at a high temperature such as 60°C.

Even in other corresponding cases, the addition of the compound having the nitrogen base can considerably increase the percent DHPO retention.

The present invention can be most effectively applied also to stabilization, separation and purification of hydroperoxides in processes for obtaining resorcinol and hydroquinone from alkylbenzenes.

Now, the present invention will be described by way of Example. In Example, parts are all by weight.

EXAMPLE

Stabilization and extraction of DHPO were carried out at the same time in the present Example.

1.5 parts of ammonia was added to 300 parts of an aqueous 8% caustic soda solution containing 12.3% DHPO, and the solution was subjected to extraction with 600 parts of methylisobutylketone at 60°C for 90 minutes through three counter-current contact stages. Similar extraction operation was carried out in another run under the same conditions except that only the extraction time was changed to 300 minutes.

Through a series of these extraction operations, DHPO was classified into the following three groups.

1. DHPO contained in methylisobutylketone as the extracting agent (extract DHPO)
2. DHPO remaining in the original aqueous alkaline solution (water layer DHPO)
3. Decomposed DHPO (loss DHPO)

Proportions in said three groups 1, 2 and 3 of DHPO contained in the original aqueous caustic soda solution are given in Table 1 as a result of the operation.

COMPARATIVE EXAMPLE

Similar extraction operation was carried out under the same conditions as in Example for the same solution without adding ammonia to the solution. The results are given in Table 1.

Table 1

| Extraction Time | Runs | Extract DHPO (%) | Water Layer DHPO (%) | Loss DHPO (%) |
| --- | --- | --- | --- | --- |
| 90 min. | Example | 90 | 9 | 1 |
|  | Comp. Ex. | 88 | 5 | 7 |
| 300 min. | Example | 89 | 7 | 4 |
|  | Comp. Ex. | 53 | 4 | 43 |

As is apparent from Table 1, DHPO can be extracted and recovered in good yield without any influence upon the extraction time when ammonia is added to the solution.

The water layer DHPO is subjected to reextraction as the recycle caustic component, and is not a substantial loss.

What is claimed is:

1. A process for stabilizing dihydroperoxides of dialkyl aromatic hydrocarbons of the formula

wherein $R_1$ and $R_2$ represent alkyl groups of three to four carbon atoms, in the process for separating said dihydroperoxides from an aqueous alkaline solution of hydroperoxides containing the dihydroperoxides by extraction with an organic solvent, which comprises adding to said aqueous alkaline solution prior to extraction a compound selected from the group consisting of ammonia, aniline, toluidine, diphenylamine, N-methylaniline, N,N-dimethylaniline, benzylamine, α-phenylethylamine, triethylamine, pyridine and urea, the amount of said compound being 0.01 to 1% by weight based on the weight of said aqueous alkaline solution.

* * * * *